(12) United States Patent
Hjelle et al.

(10) Patent No.: US 6,615,695 B1
(45) Date of Patent: Sep. 9, 2003

(54) ALTERNATIVE FABRICATION METHOD FOR SPIRAL ELECTRODES

(75) Inventors: Mark A. Hjelle, White Bear Lake, MN (US); Jon M. Ocel, New Brighton, MN (US); James T. Gates, Maple Grove, MN (US); Randolph Ahnen, Bessemer, MI (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/604,455

(22) Filed: Jun. 27, 2000

(51) Int. Cl.[7] ................................................. B26D 3/11
(52) U.S. Cl. .......................... 82/1.11; 83/53; 83/880; 409/76
(58) Field of Search ........................ 83/22, 24, 53, 83/154, 177, 861, 875, 879, 880; 607/115, 116, 122; 600/372; 470/57, 58, 8, 9, 10; 76/108.1; 82/1.11, 110; 409/48, 76, 77

(56) References Cited

U.S. PATENT DOCUMENTS

| | | | | |
|---|---|---|---|---|
| 2,533,311 A | * | 12/1950 | Chelborg et al. .............. 83/177 |
| 3,241,452 A | * | 3/1966 | Wellard ........................ 409/70 |
| 3,985,848 A | * | 10/1976 | Frische et al. ................. 83/177 |
| 4,081,892 A | * | 4/1978 | Mercer .......................... 83/53 |
| 4,152,958 A | * | 5/1979 | Bogert ......................... 83/177 |
| 4,481,953 A | | 11/1984 | Gold et al. ................... 128/786 |
| 4,787,178 A | * | 11/1988 | Morgan et al. ................ 83/177 |
| 4,817,634 A | | 4/1989 | Holleman et al. ........... 128/784 |
| 4,860,769 A | | 8/1989 | Fogarty et al. .............. 128/786 |
| 4,865,037 A | | 9/1989 | Chin et al. ................... 128/419 |
| 4,932,407 A | | 6/1990 | Williams ...................... 128/419 |
| 5,042,143 A | | 8/1991 | Holleman et al. ............. 29/825 |
| 5,044,374 A | | 9/1991 | Lindemans et al. ......... 128/784 |
| 5,090,422 A | | 2/1992 | Dahl et al. ................... 128/784 |
| 5,265,623 A | | 11/1993 | Kroll et al. .................. 607/122 |
| 5,439,485 A | | 8/1995 | Mar et al. .................... 607/119 |
| 5,488,761 A | * | 2/1996 | Leone ........................... 29/2.1 |
| 5,538,056 A | * | 7/1996 | Thoma .......................... 83/15 |
| 5,599,223 A | * | 2/1997 | Mains, Jr. ..................... 83/53 |
| 5,605,492 A | * | 2/1997 | Klingel ........................ 83/177 |
| 5,728,149 A | | 3/1998 | Laske et al. ................. 607/122 |
| 5,762,538 A | * | 6/1998 | Shaffer ........................ 408/144 |
| 5,927,129 A | * | 7/1999 | Thoms et al. .................. 83/53 |
| 5,941,466 A | * | 8/1999 | Alba et al. .................... 83/53 |
| 6,101,912 A | * | 8/2000 | Sanders et al. ................ 83/53 |
| 6,103,049 A | * | 8/2000 | Batdorf ....................... 83/177 |
| 6,197,065 B1 | * | 3/2001 | Martin et al. ............ 623/23.17 |
| 6,438,427 B1 | * | 8/2002 | Rexhausen et al. ......... 607/119 |

OTHER PUBLICATIONS http://www.synova.ch/technology/microjet/index.html, "A bright idea that puts the competition in the shade.", (Mar. 2000).

* cited by examiner

*Primary Examiner*—Kenneth E. Peterson
(74) *Attorney, Agent, or Firm*—Girma Wolde-Michael; Michael C. Soldner

(57) ABSTRACT

Spiral electrodes and similar structures are manufactured using a high-pressure fluid stream. Specifically, spiral electrodes are made from tubular structures by using a high-pressure water stream to precisely cut, or etch spirals of predetermined geometries to conform to a particular current distribution and conduction requirements. In an embodiment, the high-pressure water stream is tangentially and rotatably oriented against a rotating and translating tubular element. The tangential orientation enables limited cutting or etching of the tubular surface that is only in direct contact with the high pressure stream. Various geometries and spiral structures could be formed by managing the pressure and rotation of the high-pressure water stream source and the rotation and translation of the tubular element.

19 Claims, 4 Drawing Sheets

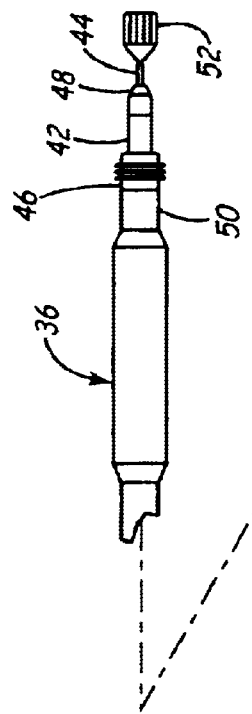
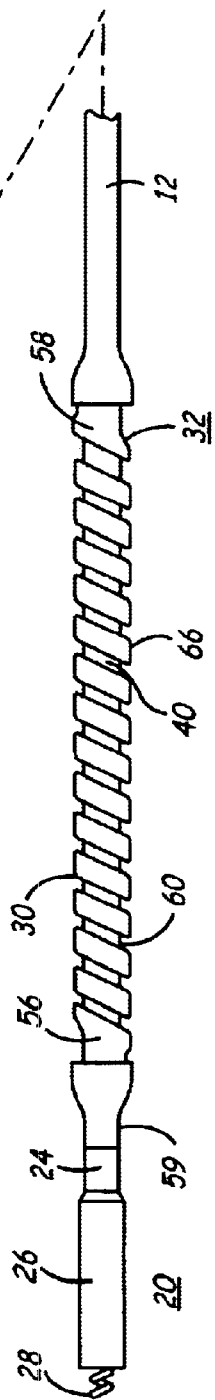
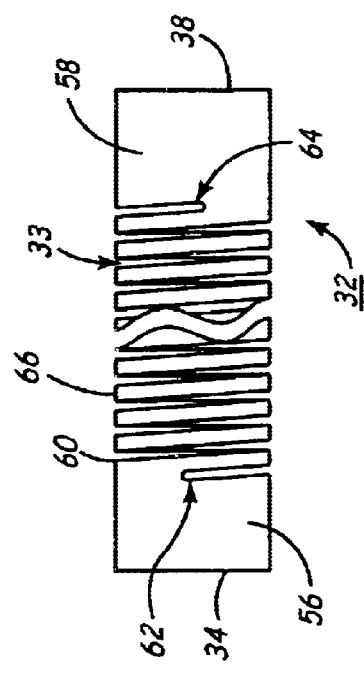
FIG. 2
FIG. 3

ALTERNATIVE FABRICATION METHOD FOR SPIRAL ELECTRODES

FIELD OF THE INVENTION

The present invention relates to implantable medical devices, such as stimulators and leads generally, and more particularly to the fabrication of spiral coil electrodes, spiral stents and other tubal spiral structures.

BACKGROUND OF THE INVENTION

Currently available implantable ventricular defibrillators typically employ epicardial or subcutaneous patch electrodes, alone, or in conjunction with one or more endocardial leads equipped with one or more electrodes disposed within a heart chamber or blood vessel. Ventricular defibrillation is typically effected with at least one electrode extending along an endocardial lead body disposed within the right ventricle and one or more additional defibrillation electrodes disposed outside the right ventricle to provide two or more defibrillation current pathways through the chamber of the heart to be defibrillated. Other endocardial defibrillation leads for transvenous introduction and positioning in the right atrium and/or superior vena cava, the coronary sinus, the right outflow track or other locations in proximity to the heart have been disclosed in the prior art, including commonly assigned U.S. Pat. No. 4,932,407 to Williams.

Many versions of elongated defibrillation electrodes on a variety of endocardial lead body configurations have also been disclosed in prior patents and literature and employed clinically in patients. The requirements of an endocardial defibrillation electrode include a cross-section size and flexibility sufficient to enable transvenous introduction and withstand chronic flexing in situ. Additionally, a metal alloy exhibiting high bio-compatibility for chronic implantation, low electrical resistance per unit cross-section area of the metal alloy, the capability of providing a relatively large exposed surface area to reduce impedance off the system and distribute the electrical current of the defibrillation shock in a desired pathway in relation to the vessel or chamber of implantation, ease of manufacture, and high reliability are also required. The combination of the selection of materials, design of the electrode configuration and the supporting lead body, and the construction methods employed contribute to achieving these requirements.

After many years of development, the typical endocardial lead defibrillation electrode is configured as an elongated, bio-compatible wire of high conductivity that is spirally space wound or close wound about the lead body for a length appropriate for the intended use. The spacing of the coil turns retains flexibility of the lead body along the length of the electrode and further distributes the electrode surface area along the length thereof. The wire cross-section is typically circular, as shown in U.S. Pat. No. 5,042,143 to Holleman et al., or rectangular, as shown in U.S. Pat. No. 4,481,953 to Gold et al., U.S. Pat. No. 5,090,422 to Dahl et al., and U.S. Pat. No. 5,265,623 to Kroll et al., although other wire configurations, e.g. the wrapped coils of U.S. Pat. No. 5,439,485 to Mar et al., have also been disclosed. The coiled wire electrode may be formed of a single wire or in a multi-filament configuration of interlaced wires as shown in certain embodiments of the '485 patent. The coiled wire turns are typically partially embedded into the underlying lead body insulation to mechanically stabilize the exposed coil turns and direct t,he defibrillation current outward of the lead body.

In addition, various types of epicardial defibrillation leads having multiple coiled wire electrodes emanating from a common connection or connections with the defibrillation lead conductor have been disclosed as shown in certain embodiments of the above referenced '422 and '485 patents and in U.S. Pat. No. 4,860,769 to Fogarty et al., U.S. Pat. No. 4,865,037 to Chin et al., U.S. Pat. No. 4,817,634 to Holleman and U.S. Pat. No. 5,044,374 to Lindemans et al. In the '634 and '374 patents, a "patch" lead is depicted having four electrically parallel, branching coiled wire conductors arrayed in a flat supporting patch. The winding pitch of the wire coils is increased in the outermost two branches as compared to the innermost two branches, depicting an arrangement that would have the effect of increasing the electrode surface area along the periphery of the patch, where the current density is typically concentrated in such electrodes.

The exposed defibrillation electrode must be electrically and mechanically attached at one or more points to a defibrillation lead conductor that extends proximally to la connector at the proximal end of the lead body. Typically, the defibrillation lead conductor is a coiled wire conductor, although straight wires of stranded wire filaments are also used. In either case, one end or both ends of the spiral wound defibrillation electrode wire are attached to the lead conductor extending to the proximal end. The attachment(s) require a number of separate parts, and the attachment sleeves, cores and crimps involved may result in a cumbersome and unduly enlarged connection.

As shown in the '143 and '485 patents, the coiled wire ends are attached to sleeves by welding, crimping or the like, and at least one of the sleeves is adhered to the internal coiled wire conductor. In the '953 patent, the ends of the defibrillation electrode wire coil are schematically shown directly connected inside the lead body to the ends of internally disposed straight defibrillation lead conductors. In practice, however, additional parts are needed to make a reliable connection With operable lead conductors.

The '623 patent discloses the electrical connection of a stranded wire filament cable, defibrillation lead conductor at a central point along the length of an exposed wire ribbon defibrillation electrode. The central connection purportedly alters the electrical field and current distribution of a defibrillation shock applied to the defibrillation electrode with respect to the heart vessel or chamber. The wire ribbon is formed of a continuous rectangular cross-section band wound over a lead body outer insulation sheath in a spiral and between a pair of separate electrode end rings. The separate end rings appear to restrain longitudinal expansion of the wire ribbon electrode.

Further, a commercially available Endotak® endocardial defibrillation lead is constructed with similar ribbon wire electrode and end caps that are welded to the ends of the wire ribbon. The electrical connection to the defibrillation lead conductor is effected at one or both end caps. The '623 patent is directed to improving, the electrical current distribution of such an electrode design by decreasing the edge effect current concentrations that can occur at the ends, particularly at the end(s) where the electrical connection(s) to the defibrillation lead conductor is made. It is asserted that such concentrated current densities may damage blood vessels of heart tissue in their vicinity.

A novel approach is disclosed in U.S. Pat. No. 5,728,149 issued to Laske, et al, in which the defibrillation electrode is fabricated of a single tubular member of bio-compatible, electrically conductive material that has the appearance of a band wound around a central point. A plurality of spiral slits is formed in the tubular member thereby forming a plurality of spiral bands integrally attached to the first and second end bands, respectively. The pitch and/or width of the spiral slit bonding including any intermediate connection band may be altered in order to accommodate the electrical connection with the defibrillation lead conductor. This invention, as it relates to the embodiments, requires that the electrical connections may be made directly by welding, crimping or the like to adhere the annular end or intermediate connection band(s) or the intermediate spiral band to the underlying defibrillation lead conductor without any additional parts.

Current fabrication methods to produce the coils in a tubular member include Electron Discharge Machining of the tube stock, coil winding from wire, and milling of the tube stock. These methods are either expensive, design limiting, or alter the natural material properties of the electrode. Other methods include laser or water jet cutting. In both of these fabrication processes, the cutting apparatus is positioned in a superior and central position over the piece to be cut or etched. Because the objective in manufacturing a small diameter implantable electrode is to cut through only one wall of the tubular material, the superior and central positioning of the laser or water jet over the tube makes it impossible to protect the opposite wall from being cut as well. Thus a new approach to the positioning of the jet is necessary.

Accordingly, it continues to be desirable to simplify transvenous defibrillation lead body construction and to make the resulting lead more reliable for long term implantation. Reduction of piece-separate parts and efficient assembly steps in the attachment of the defibrillation electrode with the defibrillation lead conductor are some of the desired features which enhance reliability and quality.

SUMMARY OF THE INVENTION

The present invention is generally directed to an improved fabrication process involving the use of a high-pressure water jet to cut or etch in order to form spiral bands in a coiled defibrillation lead. The invention accomplishes this enhancement by strategically positioning and dynamically adjusting a high-pressure water jet to an outside wall of a tubular member. Such positioning allows the high-pressure water jet to make contact only with the proximate outside wall of the tube during the cutting or etching process. This method prevents cutting or etching of the opposing wall of the tubular member. Simultaneous rotation and translation of the tubular member across the discharge path of the water jet enables to form a spiral structure with a specified pitch along the desired length of the tubular member. Etching and cutting such tubes is more economical than creating a coil of drawn wire that must, in turn, be electrically connected to end bands of the coil. Moreover, the high-pressure water jet will riot anneal, warp or otherwise alter the chemical or physical constitution of the material from which the tubular member is made.

The present invention provides a fabrication process for preferably endocardial defibrillation electrodes. This process, however, is not limited to the fabrication of such electrodes and may also be used in the fabrication of implantable spiral stents, spiral structures and similar spring-like homogenous units.

BRIEF DESCRIPTION OF THE DRAWINGS

FIG. 2 is a plan view of one embodiment of a defibrillation lead having a tubular member cut or etched into one or more spiral bands between integral end bands attached to a defibrillation lead conductor.

FIG. 3 is a side view of one embodiment of the tubular member of FIG. 2 that has been cut into a single band having a fixed pitch and spiral bandwidth integrally attached to the end bands thereof.

DETAILED DESCRIPTION OF THE DRAWINGS

Figure 1:
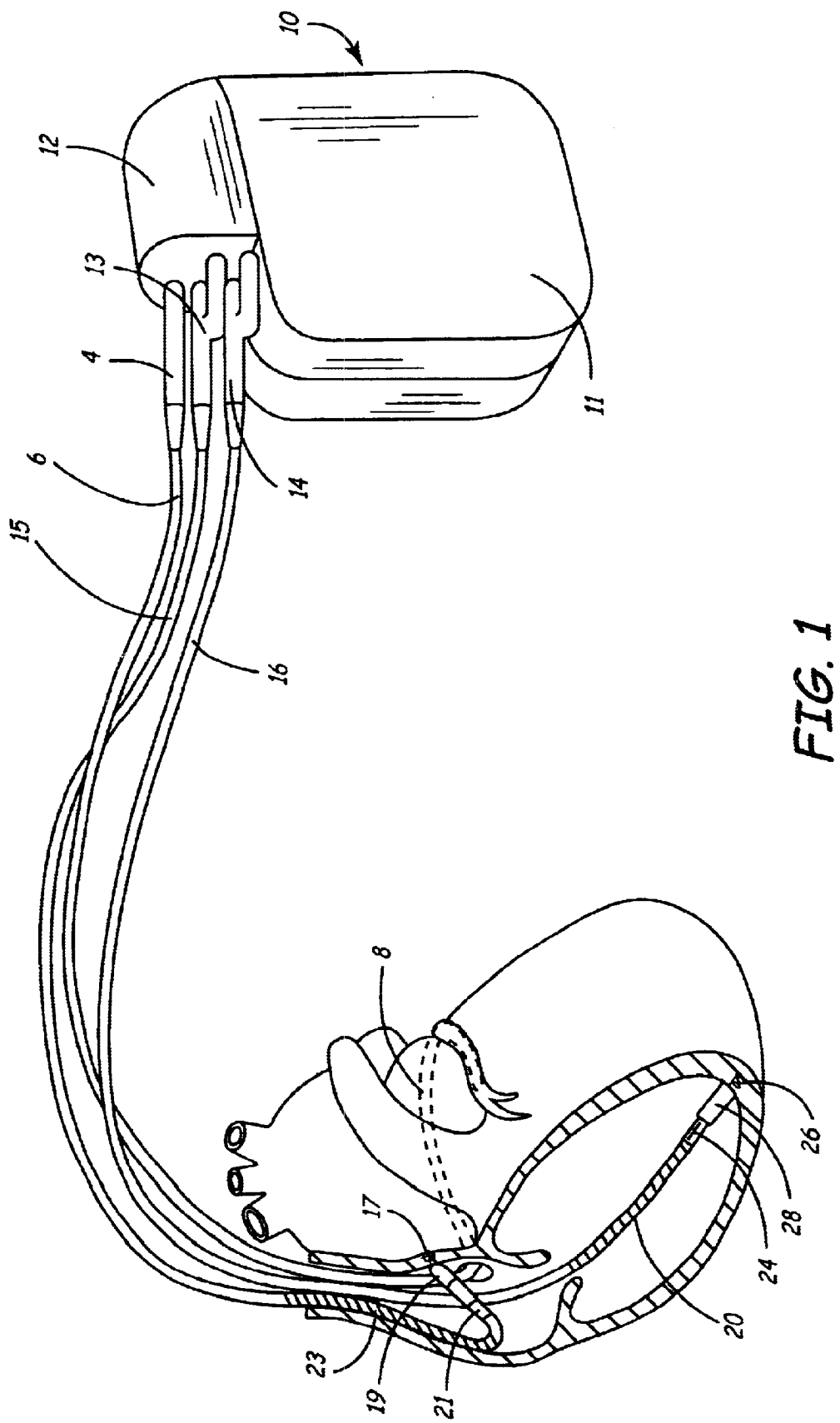
FIG. 1 illustrates an embodiment of an implantable pacemaker/cardioverter/defibrillator of a type appropriate for use in practicing the present invention, in conjunction with a human heart.

FIG. 1 illustrates a defibrillator and lead set that may embody an electrode fabricated by the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coiled defibrillation electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 that carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding generally to the structure of the ventricular lead. Located adjacent to the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coiled defibrillation electrode 23 is provided, proximal to electrode 21 and coupled to the third conductor within the lead body 15. Electrode 23 preferably is 5 cm in length or greater and is configured to extend from the SVC toward the tricuspid valve. At the proximal end of the lead is a bifurcated connector 13 that carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using an insulative coating, for example parylene or silicone rubber, as is currently employed in some unipolar cardiac pacemakers. However, the outward facing portion may instead be left uninsulated, or some other separation means between insulated and uninsulated portions may be employed. The uninsulated portion of the housing 11 optionally serves as a subcutaneous defibrillation electrode, used to defibrillate either the atria or ventricles. Other lead configurations and electrode locations may, of course, be substituted for the lead set illustrated. For example, atrial defibrillation and sensing electrodes might be added to either the coronary sinus lead or the right ventricular lead instead of being located on a separate atrial lead, allowing for a two-lead system.

FIG. 2 illustrates an overall view of a defibrillation lead 10 having an embodiment of a defibrillation electrode 30 fabricated in accordance with the present invention. Specifically, electrode 30 includes a variable pitch formed thereon to manage a particular current distribution. The substantially straight distal end section of the defibrillation lead 10 is provided with a pace/sense electrode assembly 20 including an extendable substantially helical, pace/sense electrode 23, mounted retractably within an insulating electrode head 26, and a ring shaped pace/sense electrode 24 forming a pace/sense electrode pair. A distal outer insulating sleeve 59 overlaps and stabilizes the distal end of the elongated, exposed defibrillation electrode 30 and terminates just proximal to the ring-shaped pace/sense electrode 24.

FIG. 2 further illustrates the proximal connector end of defibrillation lead 10 having connector assembly 36 attached to a proximal outer insulating sheath 12. As depicted, electrical connector assembly 36 is a tri-polar in-line connector, but may be a bifurcated or trifurcated connector assembly of the type shown in the above-referenced '407 and '623 patents. The depicted electrical connector assembly 36 includes connector ring surfaces 42 and 50 and a hollow lumen, rotatable connector pin 44. Insulating segments 46 and 48 separate connector ring surfaces 42 and 50 and connector pin 44 and are each provided with a plurality of sealing rings for sealing the connector within the connector block of an associated implantable pacemaker/cardioverter/defibrillator.

Turning to the construction of the defibrillation electrode 30, in accordance with the present invention, it is formed of an integral tubular member 32 of bio-compatible, electrically conductive material, e.g. platinum, platinum alloy, a platinum coated titanium or tantalum conductor. The integral tubular member 32 may take any of several configurations as shown in FIGS. 2, 3, 4, 7, 8, and 9 of the '149 patent and combinations and variations thereof and is electrically coupled to the defibrillation lead conductor, which may take forms other than the coiled wire conductor described above, through integral connection band or bands. As described below, the particular lead body and lead conductor configuration may vary considerably from the above-described FIG. 2 embodiments of defibrillation lead 10.

FIG. 3 shows tubular member 32 which has a first or distal tube end 34 and a second or proximal tube end 38 and a lumen 33 having an inside diameter selected to fit over the lead body and particularly, a separate, intermediate outer sheath 40 of FIG. 2 of the lead body insulating the internally disposed defibrillation lead conductor 14 of FIG. 1. A spiral slit 60 is formed therein extending from first and second slit end points 62 and 64, spaced from the first and second ends 34 and 38, respectively, thereby forming at least one spiral band 66 integrally attached to the first and second annular end bands 56 and 58, respectively. Preferably, both the first and second end bands 56 and 58 can be used as connection bands to electrically connect to the defibrillation lead conductor 14 of FIG. 1.

Figure 4B:
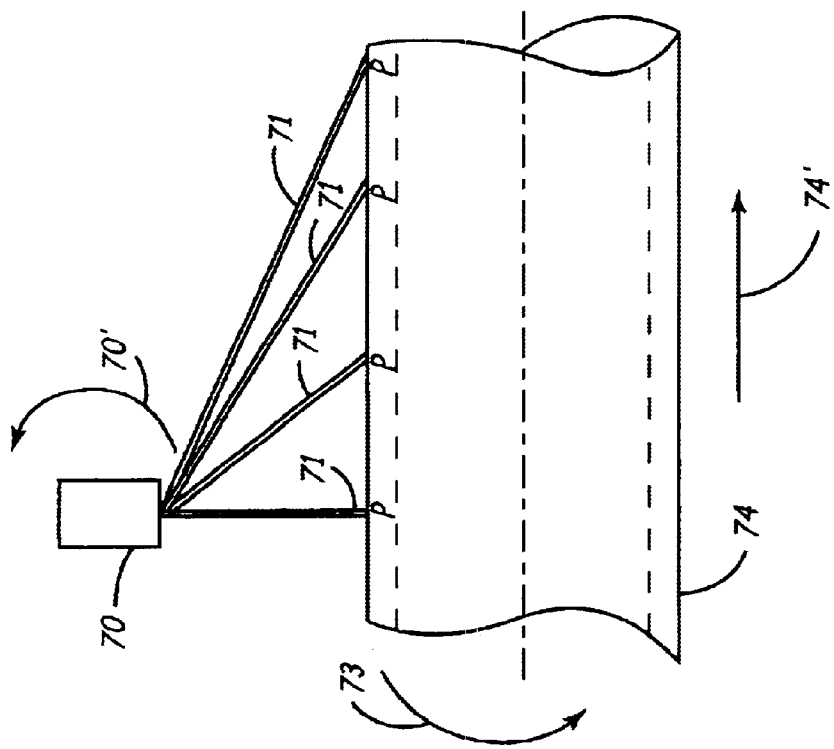
FIG. 4B is a side view of the assembly in FIG. 4A depicting the various dynamic adjustments.
Figure 4A:
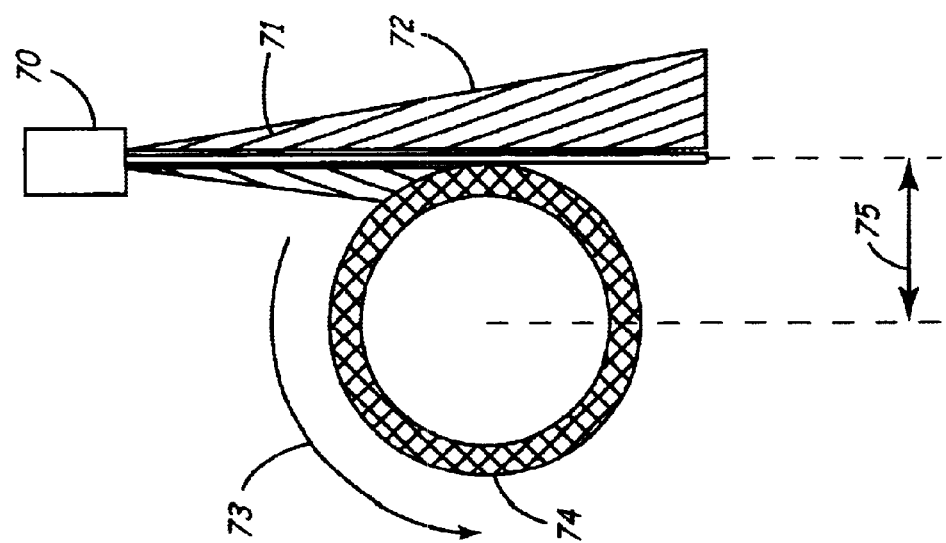
FIG. 4A is a cross sectional, end-on view of a tube being cut or etched by a water jet positioned tangentially to the tube stock.

FIG. 4A shows a cross sectional, end-on view of a nozzle 70 discharging a high-pressure water jet 71 on a tangential trajectory to cut or etch only a portion or wall of tubular member 74 being fabricated. A certain amount of water spray 72 aids in cooling the member during fabrication. The distance 75 is the space between the centers of the tubular member 74 and the high-pressure water jet 71. This distance may be varied to produce the desired pitch in the electrode coil. The rotation 73 of the tubular member 74 brings the uncut, non-etched portion of the tubular member 74 into direct contact with the high-pressure water jet oriented at pre-selected tangential position relative to tubular member 74. Thus, a continuous slit may be cut in the tubular member, as depicted in FIG. 3, by simultaneously rotating and translating tubular member 74 across the high-pressure water jet 71. This tangential fabrication approach allows the high-pressure water jet 71 to cut or etch only the surface in immediate contact with the high-pressure water jet, thereby preventing any cut or etch of the opposing wall of tubular member 74.

FIG. 4B represents a side view of the assembly in FIG. 4A. Specifically, the translational excursions of nozzle 70 are depicted at rotation 70'. High pressure water jets 71 are shown at various tangential angular points of incidence "P" as indicated. Further, the rotation of tubular member 74 and the continuous or indexed longitudinal translation are indicated by elements 73 and 74', respectively. As discussed hereinabove, the rotation 73 of tubular member 74 exposes an uncut, non-etched portion of member 74 to high-pressure water jet 71. The fluid jet could also contain an entrained abrasive slurry to effect the cutting action. Industrial grade gems (i.e. ruby) are routinely used in this application, but potentially other abrasives could be used as well. The longitudinal movement 74' is either indexed or continuous and coordinated with the dynamic condition of nozzle 70. Similarly, the rotation 70' of nozzle 70 could be dynamically adjusted to fabricate various types of spirals, for example, spiral slit 60 (see FIG. 3) may be made large or small and the pitch may be varied to create various spiral geometries. One aspect of the invention provides a uniform spiral that is formed when water jet 71 is set at a predetermined angle of incidence "P". Another aspect of the invention provides a method for generating various slit 60 configurations based on changing the thread geometry of slit 60. For example, coarse-thread, fine-thread, variable thread geometries may be made by coordinating the rotation 70' of nozzle 70, the rotation 73 and translation 74' of tubular member 74. In another aspect of the invention rotations 70', 73 and translation 74' are coordinated to provide cuts or etches of either uniform or variable slit geometries depending on expected current distribution which the spiral may conduct. Further the water jet 71 pressure may be controlled to etch or cut tubular member 74 consistent with the relative motions of nozzle 70 and tabular member 74.

Figure 5:
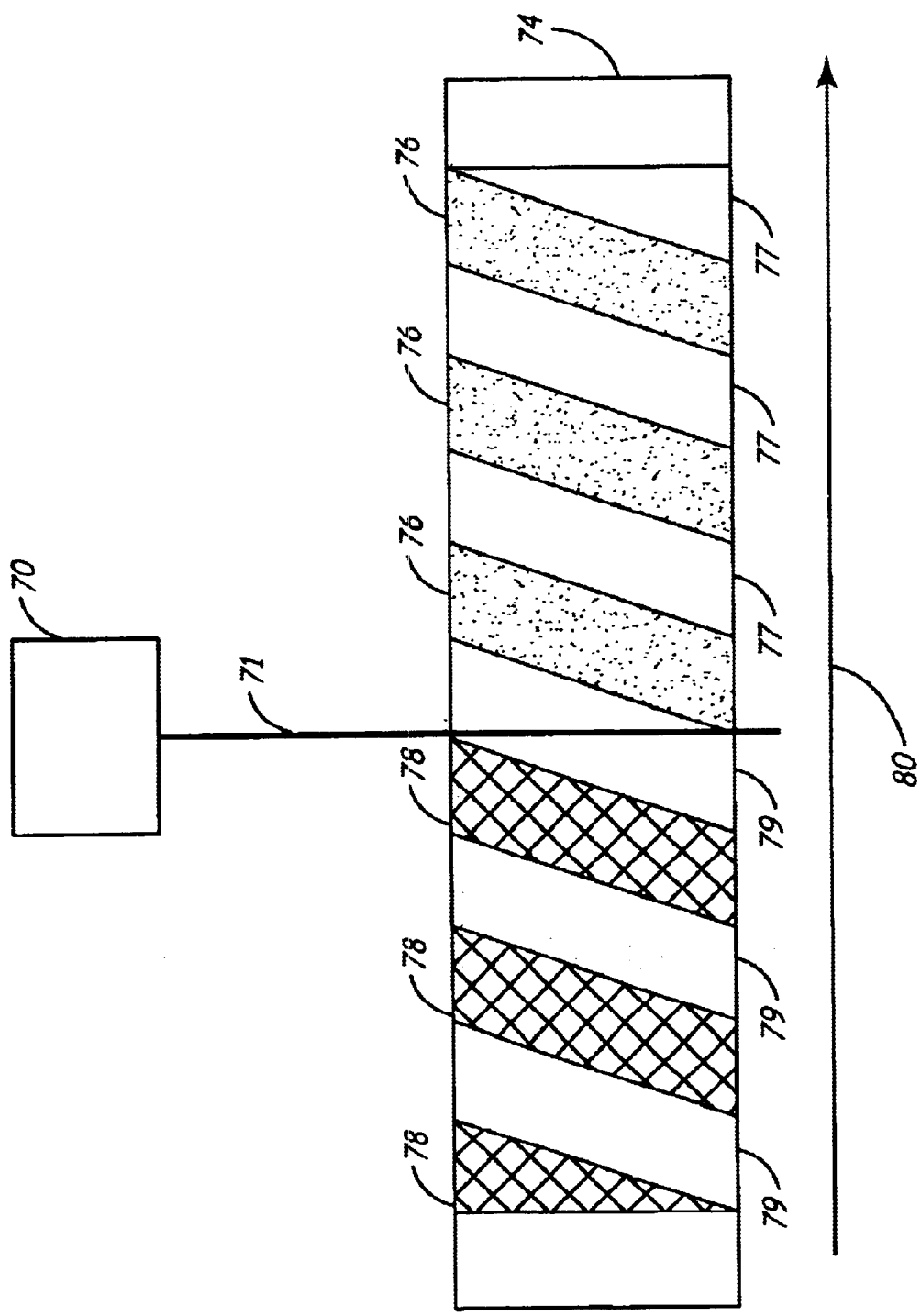
FIG. 5 is a side view of a tube that is transiting across the path of the water jet while rotating during the etching process.

FIG. 5 illustrates a cross sectional, overhead view of the cutting or etching process midway through fabrication. A nozzle 70 sends a high-pressure water jet 71 across a tubular member in a tangential manner. The tubular member is caused to rotate and advance in the direction of transit 80 across the high-pressure water jet 71. This simultaneous rotation and linear transition of the tubular member 74 across the high-pressure water jet 71 results in a band-like structure of alternating solid bands 76 and slits 77 having the specified pitch for use in a coil electrode. Exemplary bands and slits to be cut or etched are depicted in bands 78 and slits 79.

Accordingly, the present invention provides an apparatus and method for cutting or etching a coil from a metal element to yield a predetermined coil pitch. Variations in the pitch, including coarse and fine cuts or etches could be dynamically formed by adjusting one or more of the moving systems of the invention. Specifically, rotation 73 and translation 74' of tubular member 74 and rotation 70' of nozzle 70 independently or in combination may be adjusted and coordinated to cut and etch various spiral geometries to accommodate current density requirements and operations.

The preceding specific embodiments are therefore to be understood as illustrations of the many ways in which the principles of the invention may be practiced. It is understood, therefore, that other expedients known to those of skill in the art or disclosed herein may be employed without departing from the invention or the scope of the appended claims.

What is claimed is:

1. A method of cutting and etching a substantially tubular electrode, comprising the steps of:
    generating a high-pressure fluid stream;
    positioning the electrode in tangential contact with the high pressure fluid stream; and
    rotating and translating the electrode while maintaining said tangential contact with the high pressure fluid stream to provide a desired current distribution of the electrode, wherein said electrode includes a metallic material selected from the group consisting of platinum, platinum alloy, platinum coated titanium, and tantalum conductor.

2. The method of claim 1, wherein the high-pressure fluid stream is water at high pressure delivered through a nozzle.

3. The method of claim 1 wherein said tangential contact is made by maintaining the high pressure fluid stream in a fixed position.

4. The method of claim 1 wherein said tangential contact is made by rotating the high-pressure fluid stream.

5. The method of claim 1, wherein the cutting and etching is of uniform geometry.

6. The method of claim 1, wherein the cutting and etching is of non-uniform geometry.

7. The method of claim 1, wherein the high-pressure fluid stream includes a water spray cooling the electrode.

8. The method of claim 1, wherein said fluid stream is water at high pressure discharging from a nozzle and includes variable pressure adjustments to control discharge pressure and to adapt to specific cutting or etching of said electrode.

9. The method of claim 1, wherein said tangential contact relates to an immediate contact surface and the high pressure cut or etch is limited to said immediate contact surface.

10. The method of claim 1, further comprising the step of rotating the high-pressure fluid stream while maintaining said tangential contact.

11. The method of claim 1, wherein said tangential contact is maintained by keeping the high-pressure fluid stream in a fixed position.

12. A method for cutting and etching a spiral electrode for medical device applications, comprising the steps of:
    generating a high-pressure fluid stream adapted for cutting or etching the electrode;
    positioning the electrode in tangential contact with the fluid stream;
    maintaining the tangential contact between said high-pressure fluid stream and said electrode; and
    rotating and transversally moving said electrode while maintaining said tangential contact to create an electrode surface capable of providing a predetermined current density, wherein said electrode includes a metallic material selected from the group consisting of platinum, platinum alloy, platinum coated titanium, and tantalum conductor.

13. The method of claim 12 wherein said fluid stream is water at high pressure discharging from a nozzle and includes variable pressure adjustments to control discharge pressure and to adapt to specific cutting or etching of said electrode.

14. The method of claim 12 wherein said tangential contact relates to an immediate contact surface and the high pressure cut or etch is limited to said immediate contact surface.

15. The method of claim 12 further comprising rotating the high-pressure fluid stream while maintaining said tangential contact.

16. The method of claim 12 wherein said tangential contact is maintained by keeping the high-pressure fluid stream in a fixed position.

17. The method of claim 12 wherein the high-pressure fluid stream includes a water spray cooling the electrode.

18. The method of claim 12, wherein the electrode includes a lumen and the tangential contact directs the fluid stream to a first portion of the electrode so that the fluid stream does not cut or etch a second portion of the electrode opposite the first portion through the lumen.

19. The method of claim 12, further comprising the step of positioning a central axis of the electrode a distance from the fluid stream corresponding to a desired current distribution of the electrode.

* * * * *